(12) United States Patent
Hill et al.

(10) Patent No.: US 8,402,809 B2
(45) Date of Patent: Mar. 26, 2013

(54) METHOD FOR DETERMINING THE WORK REQUIRED TO EXPEL A TAMPON FROM A TAMPON APPLICATOR

(75) Inventors: Donna Rene Hill, Verona, KY (US); John David Norcom, Middletown, OH (US)

(73) Assignee: The Procter & Gamble Company, Cincinnati, OH (US)

(*) Notice: Subject to any disclaimer, the term of this patent is extended or adjusted under 35 U.S.C. 154(b) by 810 days.

(21) Appl. No.: 12/554,336

(22) Filed: Sep. 4, 2009

(65) Prior Publication Data
US 2011/0060548 A1 Mar. 10, 2011

(51) Int. Cl.
*G01N 3/56* (2006.01)
*G01N 19/02* (2006.01)
(52) U.S. Cl. .................... 73/9; 604/11; 604/15
(58) Field of Classification Search ............... 73/9, 826, 73/12.01, 12.09, 12.11, 789
See application file for complete search history.

(56) References Cited

U.S. PATENT DOCUMENTS

| | | | |
|---|---|---|---|
| 4,675,834 A * | 6/1987 | Furuse | 702/51 |
| 5,601,530 A | 2/1997 | Nielsen et al. | |
| 6,652,477 B2 * | 11/2003 | Karapasha et al. | 604/14 |
| 7,166,085 B2 * | 1/2007 | Gann et al. | 604/11 |
| 7,213,466 B2 * | 5/2007 | Osborn et al. | 73/824 |
| 2005/0273037 A1 * | 12/2005 | Osborn et al. | 604/15 |
| 2008/0167597 A1 | 7/2008 | Dougherty | |

* cited by examiner

*Primary Examiner* — Lisa Caputo
*Assistant Examiner* — Roger Hernandez-Prewitt
(74) *Attorney, Agent, or Firm* — Andrew J. Hagerty

(57) ABSTRACT

A method and apparatus for determining the work required to expel a tampon from a tampon applicator having a barrel containing the tampon and a plunger for expelling the tampon from the barrel. The method includes the steps of selecting and applying an applicator gripping test force to a grip zone on the barrel of the tampon applicator and selecting a tampon expulsion test rate and applying a force to the plunger sufficient to expel the tampon from the barrel of the tampon applicator at the selected tampon expulsion test rate. Further, the method includes the step of calculating the force on the plunger required to expel the tampon from the barrel at the selected tampon expulsion test rate as a function of the distance the tampon travels during expulsion.

15 Claims, 4 Drawing Sheets

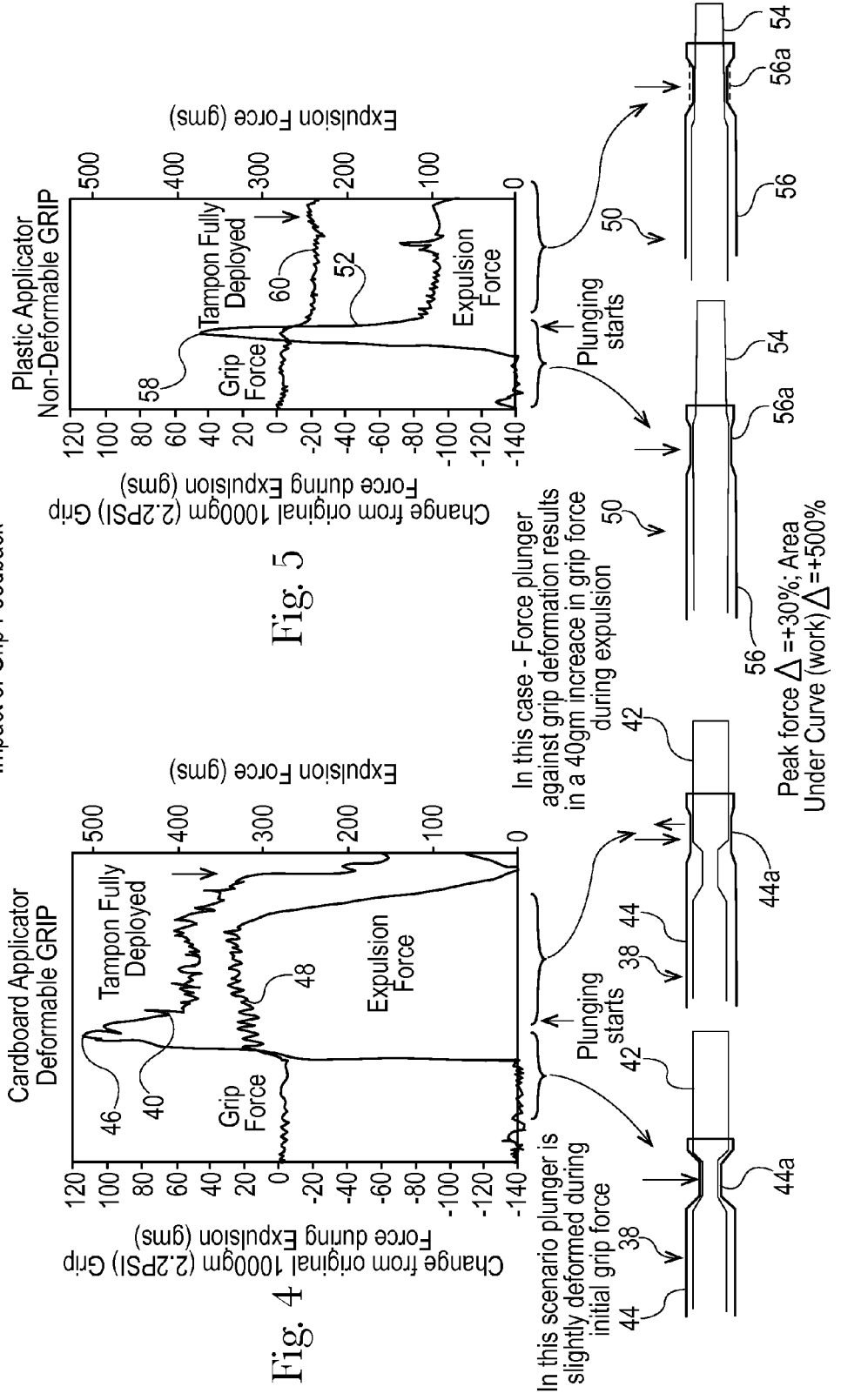

METHOD FOR DETERMINING THE WORK REQUIRED TO EXPEL A TAMPON FROM A TAMPON APPLICATOR

FIELD OF THE INVENTION

The present invention relates generally to methods and apparatuses for testing the performance of a tampon applicator during the expulsion of a tampon and, more particularly, to a method and apparatus for determining the work required to expel a tampon from a tampon applicator in a manner which correlates to the level of comfort perceived during use.

BACKGROUND OF THE INVENTION

Tampon applicators are formed of both paperboard and plastic, and they typically have a barrel and plunger used for expelling a tampon through an insertion end of the barrel into a vaginal cavity by applying a force to a finger engaging end of the plunger. Such tampon applicators have taken many different forms in an effort to satisfy the need to provide for the proper and comfortable delivery of a tampon. To this end, it is recognized as important for the tampon applicator to incorporate suitable design features making it possible to use the applicator for delivery of the tampon with a minimum of perceived discomfort or effort by the consumer.

In an effort to achieve these results, many different tampon applicators have been proposed which present a wide variety of features. However, despite these efforts, there are still shortcomings which remain to be addressed. Generally, these shortcomings relate to the inability of known tampon applicators to fully and satisfactorily address the overall comfort of the user.

Among the shortcomings in existing tampon applicators is providing a secure, comfortable grip at the gripping end of the barrel. It is also recognized that the finger engaging ends of the plungers in existing tampon applicators often are found to be less than fully adequate for applying the right amount of pressure to the plunger in a manner that ensures the proper and comfortable delivery of the tampon. Further, the barrel and plunger of existing tampon applicators have not always provided for smooth, stabilized relative sliding movement.

In addition, the insertion end of the barrel on many existing tampon applicators is formed to have a plurality of flexible petals defined by slits where the petals can open during tampon insertion and then close for withdrawal of the barrel. Thus, when a force is applied to the finger engaging end of a plunger, the plunger engages the tampon and moves it forward in the barrel until the tampon engages the flexible petals. After the tampon has engaged the flexible petals, the force which is applied to the finger engaging end of the plunger acts to force the petals to open to thereby enable the tampon to be inserted into the vaginal cavity of the user.

While efforts have continued to improve tampon applicators, there has been no effective method or apparatus for testing tampon applicators in a manner correlating to the level of comfort perceived during use. In fact, the conventional method of testing a tampon applicator containing a tampon has been to evaluate the expansion or compression stability of a tampon, typically composed of absorbent materials such as cotton, rayon or a combination of the two, by measuring the peak force needed to expel the tampon from the tampon applicator. In order to conduct this method of testing, it has been common to utilize an appropriately calibrated load cell for the purpose of measuring and recording the peak force required for tampon expulsion.

In particular, the conventional method of testing a tampon applicator has utilized a turret style apparatus that can accommodate a variety of cylindrical diameters within the range of diameters of current tampon applicators. The apparatus is used to hold the tampon applicator, typically just above the petals, with a force that will prevent slippage of the applicator when a force is applied to the plunger to expel the tampon. However, while this apparatus may measure the peak force used to expel the tampon, it does not in any way replicate the actual experience of a user so there is no correlation to the level of comfort which will be perceived during use.

It would, therefore, be desirable to have a method and apparatus for determining the work required to expel a tampon from a tampon applicator in a manner which correlates to the level of comfort perceived during use by replicating the actual experience of a user in terms of how the barrel is held and the plunger is depressed during insertion of a tampon into the vaginal cavity.

SUMMARY OF THE INVENTION

While it is known to utilize a method and apparatus for testing a tampon applicator having a barrel containing a tampon and a plunger disposed for sliding movement relative to the barrel for expelling the tampon, it has remained to provide a method and apparatus which overcomes the noted problems. Certain embodiments of the present disclosure provide a method and apparatus having improved features which make it possible to correlate the results achieved in testing a tampon applicator to the level of comfort which will be perceived during use. The method and apparatus not only test for the peak force reached during expulsion of the tampon, but they do so in a manner replicating the actual experience of a user, and they also test for the work required to expel the tampon and any grip flex in the grip zone on the barrel of a tampon applicator.

In certain embodiments, the method is directed to determining the work required to expel a tampon from a tampon applicator having a barrel containing the tampon and a plunger for expelling the tampon from the barrel. The method includes the steps of selecting an applicator gripping test force to be used to grip the grip zone on the barrel of the tampon applicator and selecting a tampon expulsion test rate to be used to expel the tampon from the barrel of the tampon applicator. The method also includes the steps of applying a force to the grip zone on the barrel of the tampon applicator by using the selected applicator gripping test force and applying a force to the plunger sufficient to expel the tampon from the barrel of the tampon applicator at the selected tampon expulsion test rate. Further, the method includes the step of calculating the force on the plunger required to expel the tampon from the barrel at the selected tampon expulsion test rate as a function of the distance the tampon travels during expulsion.

In addition, the method may advantageously include the step of measuring the actual gripping force used to grip the grip zone on the barrel of the tampon applicator in a clinical study of a selected number of consumers to establish a range of actual gripping forces and selecting an applicator gripping test force to be used to grip the grip zone within the range of actual gripping forces. Furthermore, the method may include the step of measuring the actual tampon expulsion rate used to expel the tampon from the barrel of the tampon applicator in a clinical study of a selected number of consumers to establish a range of actual tampon expulsion rates and selecting a tampon expulsion test rate to be used to expel the tampon within the range of actual tampon expulsion rates.

Still further, the method may advantageously include the step of determining grip flex in the grip zone on the barrel of the tampon applicator during the step of expelling the tampon by using a force monitor. Moreover, the step of determining grip flex in the grip zone on the barrel of the tampon applicator also may include thereafter using the force monitor to measure positive or negative forces at the grip zone as a result of any push back or collapse of the grip zone while the tampon is being expelled.

In addition, the step of calculating the force on the plunger as a function of the distance the tampon travels during expulsion also may advantageously include the step of measuring and recording the peak force reached during expulsion of the tampon at the selected tampon expulsion test rate. Furthermore, the step of calculating the force on the plunger as a function of the distance the tampon travels during expulsion also may include forming a curve and then measuring the area under the curve to determine the work required to expel the tampon at the selected tampon expulsion test rate.

In certain embodiments, the apparatus is directed to determining the work required to expel a tampon from a tampon applicator having a barrel containing the tampon and a plunger for expelling the tampon from the barrel, and it includes a test stand supporting a gripping device and an expulsion device. The gripping device includes a pair of movable fingers which are adapted to grip the grip zone on the barrel of the tampon applicator at a selected applicator gripping test force, and the expulsion device includes a movable rod to apply a force to the plunger sufficient to expel the tampon from the barrel at a selected tampon expulsion test rate. The apparatus also includes a sensor associated with the movable rod to measure the force on the plunger required to expel the tampon from the barrel at the selected tampon expulsion test rate as a function of the distance the tampon travels during expulsion to determine the work required to expel the tampon.

In addition, the sensor associated with the movable rod may advantageously be in communication with a device for recording the peak force reached during expulsion of the tampon at the selected tampon expulsion test rate, and it may be in communication with a plotter to form a curve wherein the area under the curve is a measure of the work required to expel the tampon at the selected tampon expulsion test rate. Furthermore, the sensor associated with the gripping device may comprise a force monitor which is capable of being set to zero after the selected applicator gripping test force is applied to the group zone on the barrel, and it may be adapted to measure positive or negative forces at the grip zone as a result of any push back or collapse of the grip zone while the tampon is being expelled from the barrel by the plunger.

BRIEF DESCRIPTION OF THE DRAWINGS

While the specification concludes with claims particularly pointing out and distinctly claiming the subject matter that is regarded as the present invention, it is believed that the invention will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

FIG. 4 is a graph for a cardboard tampon applicator having a deformable grip zone in which the gripping force and the work required to expel the tampon from the tampon applicator are plotted using the apparatus of FIG. 1;

FIG. 4A is a schematic diagram illustrating the cardboard tampon applicator tested as shown by the graph of FIG. 4 showing the grip zone when the initial gripping force is applied but before force is applied to the plunger;

FIG. 4B is a schematic diagram illustrating the cardboard tampon applicator tested as shown by the graph of FIG. 4 showing the grip zone when the initial gripping force is applied and after force is applied to the plunger;

FIG. 5 is a graph for a plastic tampon applicator having a non-deformable grip zone in which the gripping force and the work required to expel the tampon from the tampon applicator are plotted using the apparatus of FIG. 1;

FIG. 5A is a schematic diagram illustrating the plastic tampon applicator tested as shown by the graph of FIG. 5 showing the grip zone when the initial gripping force is applied but before force is applied to the plunger; and FIG. 5B is a schematic diagram illustrating the plastic tampon applicator tested as shown by the graph of FIG. 5 showing the grip zone when the initial gripping force is applied and after force is applied to the plunger.

DETAILED DESCRIPTION OF THE INVENTION

Figure 1:
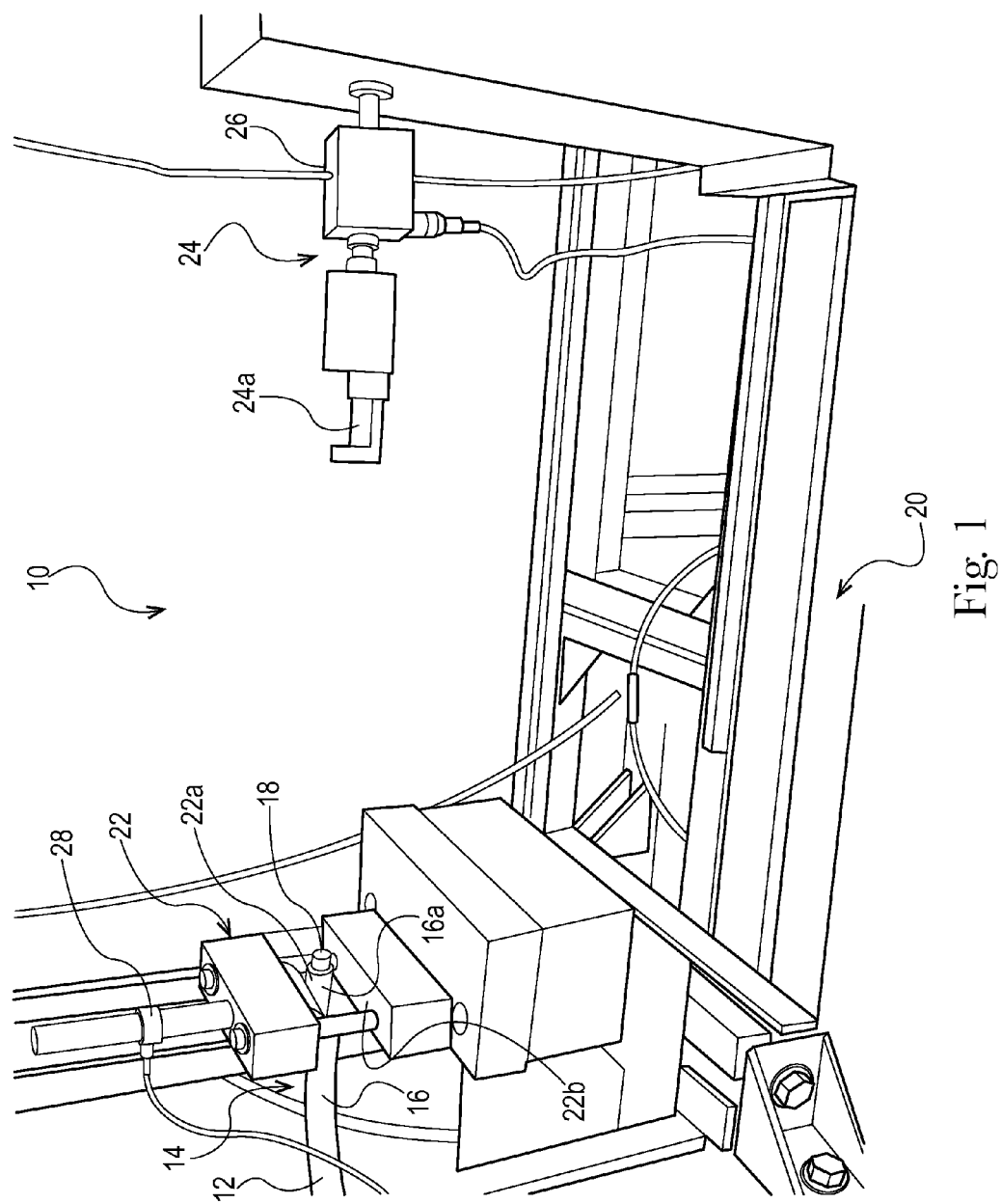
FIG. 1 is a perspective view of an apparatus for determining the work required to expel a tampon from a tampon applicator having a barrel containing the tampon and a plunger for expelling the tampon from the barrel.
Figure 2:
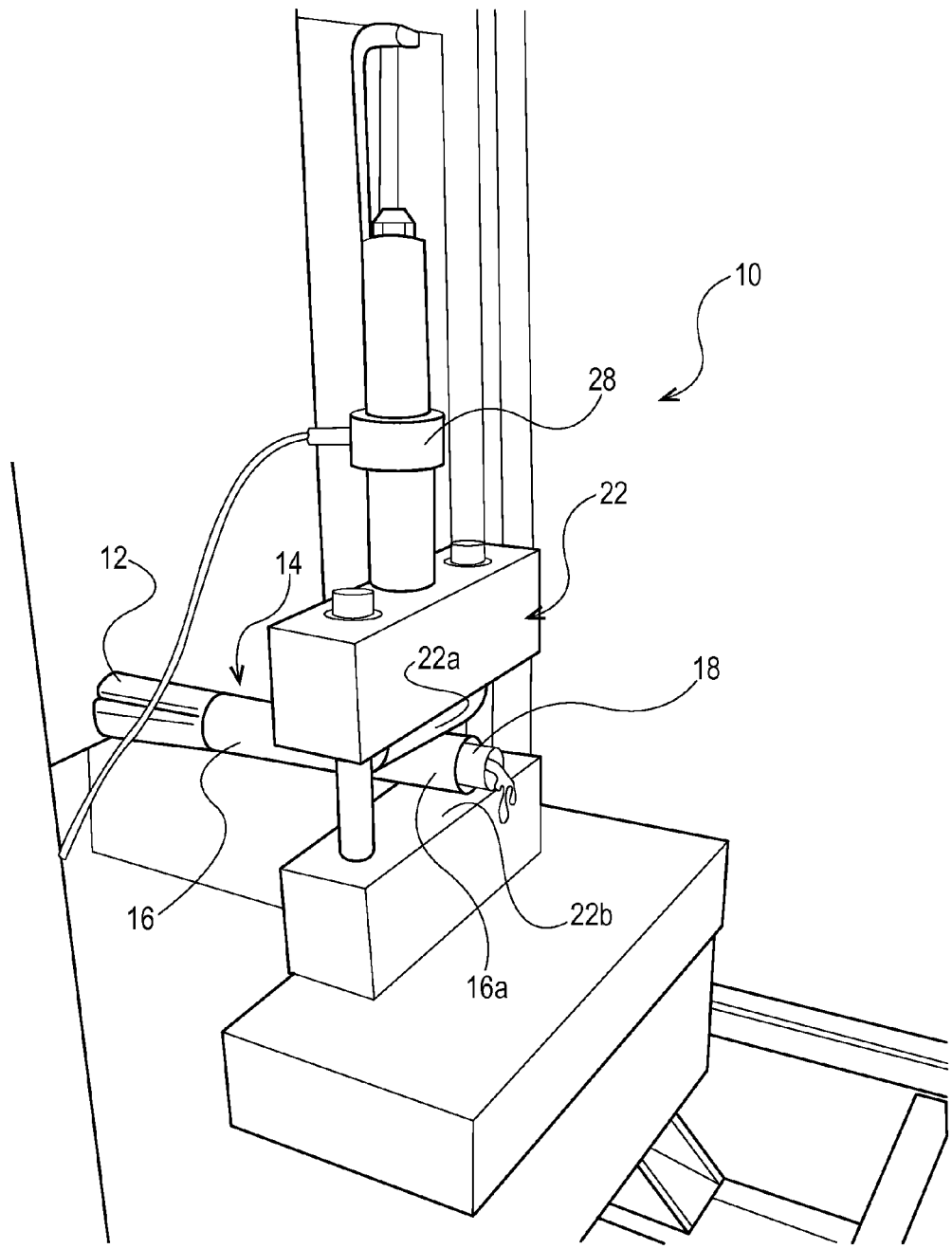
FIG. 2 is an enlarged perspective view of the portion of the apparatus of FIG. 1 provided for gripping the grip zone on the barrel of the tampon applicator and illustrating the tampon just before it is expelled from the barrel.

In accordance with the invention, and making reference to FIGS. 1 and 2, a method is disclosed for determining the work required to expel a tampon 12 from a tampon applicator 14 having a barrel 16 containing the tampon 12 and having a plunger 18 for expelling the tampon 12 from the barrel 16. The method includes the step of selecting an applicator gripping test force to be used to grip a grip zone 16a on the barrel 16 of the tampon applicator 14. It also includes the step of selecting a tampon expulsion test rate to be used to expel the tampon 12 from the barrel 16 of the tampon applicator 14. The method further includes the step of applying a force to the grip zone 16a on the barrel 16 by using the selected applicator gripping test force. It also includes the step of applying a force to the plunger 18 sufficient to expel the tampon 12 from the barrel 16 of the tampon applicator 14 at the selected tampon expulsion test rate. Further, the method for determining the work required to expel the tampon 12 includes the step of calculating the force on the plunger 18 which is required to expel the tampon 12 from the barrel 16 at the selected tampon expulsion test rate as a function of the distance the tampon 12 travels during the expulsion event.

In addition, the method may advantageously include the step of measuring the actual gripping force used to grip the grip zone 16a on the barrel 16 of the tampon applicator 14 in a clinical study of a selected number of consumers to establish a range of actual gripping forces and selecting an applicator gripping test force to be used to grip the grip zone 16a within the range of actual gripping forces. Furthermore, the method may include the step of measuring the actual tampon expulsion rate used to expel the tampon 12 from the barrel 16 of the tampon applicator 14 in a clinical study of a selected number of consumers to establish a range of actual tampon expulsion rates and selecting a tampon expulsion test rate to be used to expel the tampon 12 within the range of actual tampon expulsion rates.

Still further, the method may advantageously include the step of determining grip flex in the grip zone 16a on the barrel 16 of the tampon applicator 14 during the step of expelling the tampon 12 by using a force monitor. The force monitor can be set to zero or to any other suitable setting when the force is applied to the grip zone before the tampon is being expelled, and the change in force can be calculated. Moreover, the step of determining grip flex in the grip zone 16a on the barrel 16 of the tampon applicator 14 also may include the step of thereafter using the force monitor to measure positive or negative forces at the grip zone 16a as a result of any push back or collapse of the grip zone 16a while the tampon 12 is being expelled.

In addition, the step of calculating the force on the plunger 18 as a function of the distance the tampon 12 travels during expulsion also may advantageously include the step of measuring and recording the peak force reached during expulsion of the tampon 12 at the selected tampon expulsion test rate. Furthermore, the step of calculating the force on the plunger 18 as a function of the distance the tampon 12 travels during expulsion also may include forming a curve and then measuring the area under the curve to determine the work required to expel the tampon 12 at the selected tampon expulsion test rate.

Additionally, the method may advantageously include the step of repeating the steps of applying a force to the grip zone 16a on the barrel 16 of the tampon applicator 14, applying a force to the plunger 18 sufficient to expel the tampon 12 from the barrel 16 at the selected tampon expulsion test rate, and calculating the force applied to the plunger 18 as a function of the distance the tampon 12 travels during expulsion a selected number of times to determine an average, mean, or median for the work required to expel the tampon 12 from the tampon applicator 14.

An apparatus 10 is illustrated in FIGS. 1 and 2 for determining the work required to expel a tampon 12 from a tampon applicator 14. The tampon applicator 14 includes a barrel 16 containing the tampon 12, and there is a grip zone 16a on the barrel 16 of the tampon applicator 14 to be gripped during expulsion of the tampon 12. The tampon applicator 14 also includes a plunger 18 shown substantially fully inserted into the barrel 16 for expelling the tampon 12.

As shown in FIG. 1, the apparatus 10 includes a test stand 20 supporting a gripping device 22 for gripping the grip zone 16a on the barrel 16. The test stand 20 also supports an expulsion device 24 for expelling the tampon 12 from the barrel 16 when the grip zone 16a on the barrel 16 is being gripped by a pair of movable gripper fingers 22a and 22b associated with the gripping device 22. Referring to FIG. 2, the movable gripper fingers 22a and 22b are shown gripping the grip zone 16a on the barrel 16 by applying a selected applicator gripping test force.

The expulsion device 24 includes a movable rod 24a for applying a force to the plunger 18 sufficient to expel the tampon 12 from the barrel 16 of the tampon applicator 14 at the selected tampon expulsion test rate. The apparatus 10 also includes a sensor 26 such as a load cell which is operatively associated with the movable rod 24a for measuring the force on the plunger 18 required to expel the tampon 12 from the barrel 16 at the selected tampon expulsion test rate as a function of the distance the tampon 12 travels during expulsion. The sensor 26 is preferably in communication with a conventional device suitable for recording the peak force reached during expulsion of the tampon 12 at the selected tampon expulsion test rate.

The sensor 26 may also be in communication with a conventional plotter to form a curve wherein the area under the curve is a measure of the work required to expel the tampon 12 at the selected tampon expulsion test rate. There is preferably also a sensor 28 such as a load cell operatively associated with the gripping device 22 which comprises a force monitor capable of being set to zero after the selected applicator gripping test force is applied to the grip zone 16a on the barrel 16 by the gripper fingers 22a and 22b. The sensor 28 serves as a force monitor by a measuring positive or negative forces at the grip zone 16a as a result of any push back or collapse of the grip zone 16a while the tampon 12 is being expelled from the barrel 16 by the plunger 18.

Figure 3A:
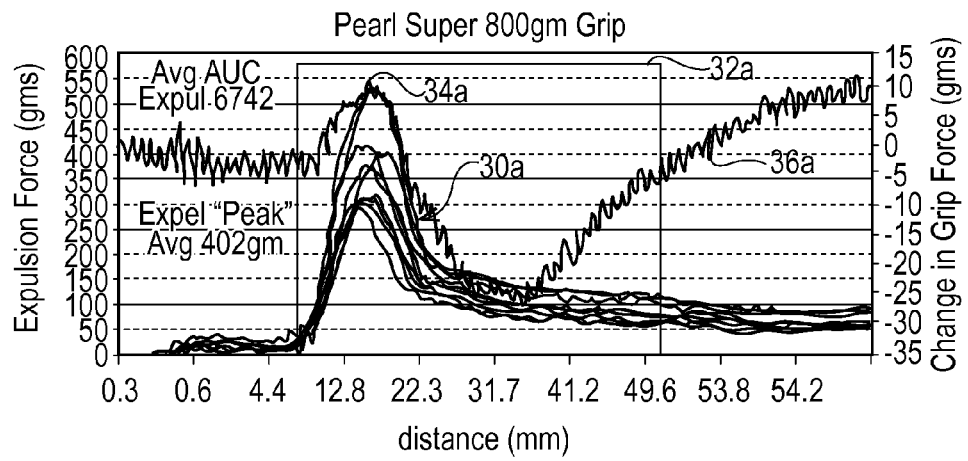
FIG. 3A is a graph for a first commercial tampon product in which the expulsion force, the gripping force and the work required to expel the tampon from the tampon applicator are plotted using the apparatus of FIG. 1.
Figure 3B:
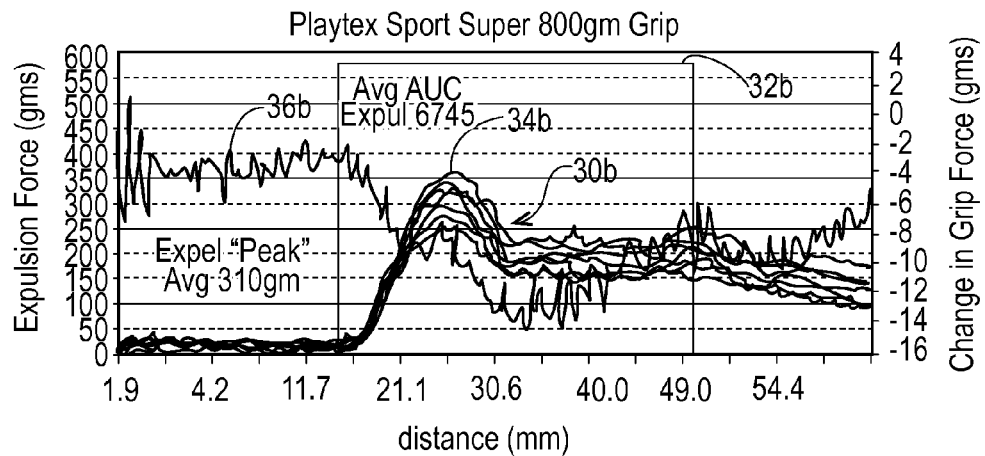
FIG. 3B is a graph for a second commercial tampon product in which the expulsion force, the gripping force and the work required to expel the tampon from the tampon applicator are plotted using the apparatus of FIG. 1.
Figure 3C:
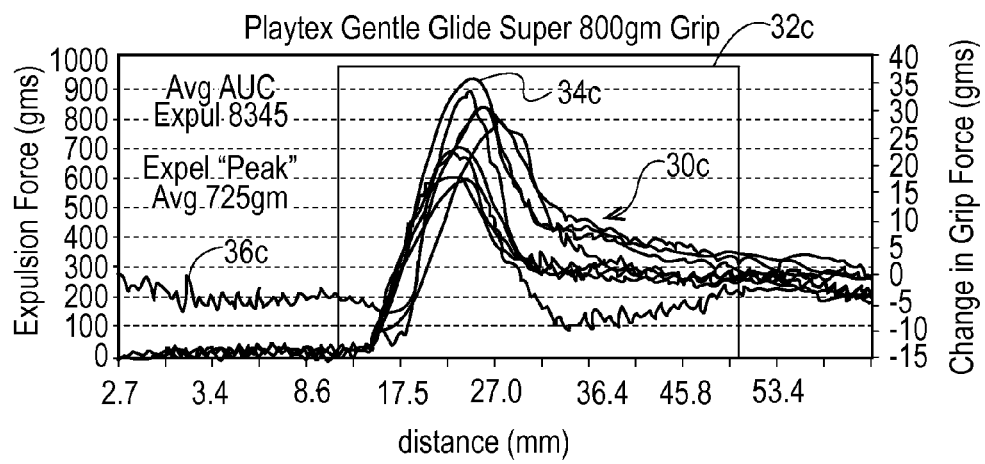
FIG. 3C is a graph for a third commercial tampon product in which the expulsion force, the gripping force and the work required to expel the tampon from the tampon applicator are plotted using the apparatus of FIG. 1.

With the method and apparatus 10, it is possible to determine the work required to expel any tampon (such as 12) from a tampon applicator (such as 14). This is demonstrated in FIGS. 3A, 3B and 3C which are actual test results for three different commercially available tampon products (Tampon Products A, B and C) wherein the multiple curves 30a, multiple curves 30b and multiple curves 30c, respectively, are actual force curves generated by the sensor 26 as a result of measuring the force on the plungers (such as 18) required to expel the tampons (such as 12) from the barrels (such as 16) of the tampon applicators (such as 14) at a selected tampon expulsion test rate as a function of the distance the tampons travel during expulsion for each of Tampon Products A, B and C. In FIGS. 3A, 3B and 3C, the multiple curves 30a, 30b and 30c, respectively, are test results on multiple samples (n=10) of Tampon Products A, B and C.

Still referring to FIGS. 3A, 3B and 3C, the boxes 32a, 32b and 32c represent the average area under the multiple curves 30a, the multiple curves 30b and the multiple curves 30c, respectively. The average area under these curves is expressed in terms of gm×mm, i.e., the average of the measured force for expelling the tampon from the barrel at the selected tampon expulsion test rate multiplied by the distance the tampon travels during expulsion. By comparing the average areas denoted by the boxes 32a, 32b and 32c, it is possible to compare the work required to expel Tampon Products A, B and C as represented in FIGS. 3A, 3B and 3C.

The sensor 26 not only provides the data to form the multiple curves 30a, 30b and 30c, but it also makes it possible to determine the peak force as at 34a, 34b and 34c during each of the multiple tests of Tampon Products A, B and C. This permits the average of the peak forces during each of the multiple tests on Tampon Products A, B and C to be determined and compared with the peak force for still other products. The sensor 28 measures any positive or negative forces at the grip zones as represented by the curves 36a, 36b and 36c as a result of any push back or collapse of the grip zones while the tampons are being expelled from the barrels by the plungers.

Referring to FIGS. 3A, 3B and 3C, it will be noted that only a single curve 36a, 36b and 36c has been shown for each of the three commercially available tampon products tested and plotted in these graphs. The actual tests on multiple samples of Tampon Products A, B and C generated multiple curves such as 36a, 36b and 36c just as these tests generated multiple curves 30a, 30b and 30c on the same samples as a result of measuring the force on the plungers required to expel the tampons from the barrels of the tampon applicators at a selected tampon expulsion test rate as a function of the distance the tampons traveled during expulsion. FIGS. 3A, 3B and 3C show only a single such curve 36a, 36b and 36c which is a representation of the average positive or negative change in grip force in order to avoid cluttering the graphs with lines.

Based upon the data generated by the sensors 24 and 28 which has been plotted in FIGS. 3A, 3B and 3C, the following table can be generated:

|  | Tampon Product A | | Tampon Product B | | Tampon Product C | |
| --- | --- | --- | --- | --- | --- | --- |
| Multiple Tests n = 10 | Avg | StdDev | Avg | StdDev | Avg | StdDev |
| Expel Peak (gm) | 402 | 92 | 310 | 35 | 725 | 112 |
| AUC Expel (gm × mm) | 6742 | 725 | 6746 | 735 | 13049 | 1957 |
| Grip Flex Max (gm) | 20.88 | 8.97 | 9.76 | 8.64 | 45.49 | 24.61 |
| Grip Flex Min (gm) | −35.91 | 5.74 | −21.77 | 5.64 | −29.36 | 14.4 |

Referring to the table, the results have been derived from the graphs for each of the three commercially available tampon products tested using the apparatus 10. It will be noted that each of Tampon Products A, B and C were tested a total of 10 times (n=10) to generate a total of 10 curves 30a, 30b and 30c and 10 curves such as the single curves 36a, 36b and 36c where the latter curves actually shown in FIGS. 3A, 3B and 3C represent the average positive or negative change in grip force determined from the actual curves developed during the actual testing of the 10 samples of Tampon Products A, B and C. From the curves 30a, 30b and 30c, the average "Expel Peak" or peak force and the average "AUC Expel" or area under the curve can be determined as well as the "StdDev" or standard deviation from the average. It will also be noted that the average and standard deviation for the "Grip Flex Max" and "Grip Flex Min", i.e., the positive and negative forces at the grip zones as a result of any push back or collapse of the grip zones while the tampons are being expelled from the barrels by the plungers can be determined from the 10 curves such as 36a, 36b and 36c generated from the actual testing of each of Tampon Products A, B and C a total of 10 times. From the table, it can be seen that Tampon Products A and B are very comparable in terms of AUC Expel and far superior to the results for Tampon Product C.

In addition, the table demonstrates that Tampon Products A and B are very comparable in terms of "Expel Peak" and, again, far superior to the results for Tampon Product C.

With regard to "Grip Flex Max" and "Grip Flex Min", the results are variable although Tampon Products A and B are far superior to Tampon Product C in terms of Grip Flex Max which is a measure of the positive force at the grip zones as a result of push back of the grip zones while the tampons are being expelled from the barrels by the plungers. This is a negative factor in terms of the perceived comfort of use of the product as is a high number for "AUC Expel" which is representative of the work and comprises the force on the plungers required to expel the tampons from the barrels at the selected tampon expulsion test rate as a function of the distance the tampons travel during expulsion. As will be appreciated, the "StdDev" or standard deviation is an indicator of the consistency of experience in using a tampon applicator in terms of the "Expel Peak" or peak force on the plunger, the "AUC Expel" or overall work required, and the "Grip Flex Max" and "Grip Flex Min" or positive and negative forces at the grip zones on the barrels.

From the foregoing, it will be understood that the method and apparatus disclosed above records the total event of tampon expulsion including the response of the grip zone during the expulsion event. As a result, the total effort or "work" required to expel the tampon from the barrel of the tampon applicator is determined using objective, measurable criteria. Moreover, the measured and recorded values for average peak force, average work, and average positive or negative forces at the grip zone closely correlate to consumer perceived comfort ratings.

In selecting an applicator gripping test force, it is desirable to measure the actual gripping force used to grip the grip zone by consumers in a clinical study. A clinical study was designed to have women expel the tampon from the barrel of the tampon applicator into the space below their body (not actually into their vaginal cavity) using their preferred ergonomic stance while having pressure sensors positioned on their fingers to record how tightly they gripped the grip zone on the barrel of the tampon applicator. It was found in this clinical study that the actual gripping force measured by the pressure sensors in PSI and converted to grams per unit area ranged from 400 to 1200 gms so the average of 800 gms was chosen as the selected applicator gripping test force for the testing of Tampon Products A, B and C reported above. The gripper fingers 22a and 22b were selected to have a working surface with similar durometer, texture and radius to fingers.

Similarly, in selecting a tampon expulsion test rate, it is desirable to measure the actual tampon expulsion test rate used by consumers in a clinical study. A clinical study was designed to have women expel the tampon from the barrel of the tampon applicator into the space below their body (not actually into their vaginal cavity) using their preferred ergonomic stance while measuring the actual tampon expulsion rate which was used to expel the tampon from the barrel of the tampon applicator. It was found in this clinical study that the actual tampon expulsion rate which was used by women during the expulsion of the tampons from the barrels of the tampon applicators fell within a determined range of actual tampon expulsion rates wherein the average rate was 80 mm/sec so this average value was chosen as the selected tampon expulsion test rate for the testing of Tampon Products A, B and C reported above.

FIG. 4 illustrates an actual test result for a commercially available tampon product having a deformable cardboard applicator 38 (see FIGS. 4A and 4B) wherein the curve 40 is the actual force curve generated by the sensor 26 as a result of measuring the force on the plunger 42 required to expel the tampon from the barrel 44 at a selected tampon expulsion test rate as a function of the distance the tampon travels during expulsion. FIG. 4 illustrates a single test on the tampon product tested. As shown in FIG. 4, the selected applicator gripping test force applied to the gripping zone 44a of the barrel 44 was 1000 gm, rather than the 800 gm gripping force used for the tests conducted on Tampon Products A, B and C (above), but this force was still well within the range of 400 to 1200 gm determined from the actual gripping force used to grip the grip zone by consumers in the clinical study discussed above.

Still referring to FIG. 4, the sensor 26 not only provides the data to form the curve 40, but it also makes it possible to determine the peak force as at 46. Similarly, it will be appreciated that the sensor 28 measures any positive or negative forces at the grip zone 44a as represented by the curve 48 as a result of any pushback or collapse of the grip zone 44a while the tampon is being expelled from the barrel 44. FIG. 4A illustrates a slight collapse during initial gripping whereas FIG. 4B illustrates a significant push back of the grip zone 44a during tampon expulsion.

FIG. 5 illustrates an actual test result for a commercially available tampon product having a non-deformable plastic applicator 50 (see FIGS. 5A and 5B) wherein the curve 52 is the actual force curve generated by the sensor 26 as a result of measuring the force on the plunger 54 required to expel the tampon from the barrel 56 at a selected tampon expulsion test rate as a function of the distance the tampon travels during expulsion. FIG. 5 illustrates a single test on the tampon product tested. As shown in FIG. 5, the selected applicator gripping test force applied to the gripping zone 56a of the barrel 56 was also 1000 gm, rather than the 800 gm gripping force used for the tests conducted on Tampon Products A, B and C (above), but this force was still within the range of 400 to 1200 gm determined from the actual gripping force used to grip the grip zone by consumers in the clinical study discussed above.

Still referring to FIG. 5, the sensor 26 not only provides the data to form the curve 52, but it also makes it possible to determine the peak force as at 58. Similarly, it will be appreciated that the sensor 28 measures any positive or negative forces at the grip zone 56a as represented by the curve 60 as a result of any pushback or collapse of the grip zone 56a while the tampon is being expelled from the barrel 56. FIG. 4A illustrates no collapse during initial gripping whereas FIG. 4B illustrates a slight collapse of the grip zone 56a during tampon expulsion.

By comparing FIG. 4 with FIG. 5, it will be understood that the commercially available tampon product having a non-deformable plastic tampon applicator 50 has a far more desirable force curve 52 when compared with the force curve 40 for the commercially available tampon product having a deformable cardboard tampon applicator 38. It is clear that the area under the curve 52 (or required work) for the non-deformable plastic tampon applicator 50 is much less than and, therefore, far superior to the area under the curve 40 (or required work) for the deformable cardboard tampon applicator 38. In addition, it will be seen that the commercially available tampon product having a non-deformable plastic tampon applicator 50 has a peak force as at 58 that is only approximately one third of the peak force as at 46 for the commercially available tampon product having a deformable cardboard tampon applicator 38.

Furthermore, by comparing the curves 48 and 60, it will be understood that the deformable cardboard tampon applicator 38 has a positive force at the grip zone 44a which is a result of pushback of the grip zone 44a (FIG. 4B) while the tampon is being expelled from the barrel 44 whereas the non-deformable plastic tampon applicator 50 has a negative force at the grip zone 56a (FIG. 5B) while the tampon is being expelled from the barrel 56.

The method and apparatus make it possible to determine the favorable nature of the non-deformable plastic tampon applicator when compared to the deformable cardboard tampon applicator during the total event of tampon expulsion. It achieves this by determining the total effort or "work" required to expel the tampon from the barrel of the tampon applicator, the peak force, and the grip zone response. By utilizing objective, measurable criteria and recording the data for multiple tests on each of these commercially available tampon products, it is possible to determine average values for these criteria which closely correlate to perceived comfort.

The dimensions and values disclosed herein are not to be understood as being strictly limited to the exact numerical values recited. Instead, unless otherwise specified, each such dimension and value is intended to mean both the recited dimension and value and a functionally equivalent range surrounding that dimension and value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for determining the work required to expel a tampon from a tampon applicator having a barrel containing the tampon and a plunger for expelling the tampon from the barrel, comprising the steps of:
   selecting a tampon expulsion test rate to be used to expel the tampon from the barrel of the tampon applicator;
   applying a force in the range of 400 to 1200 grams to the grip zone on the barrel of the tampon applicator;
   applying a force to the plunger sufficient to expel the tampon from the barrel of the tampon applicator at the selected tampon expulsion test rate; and
   calculating the force on the plunger required to expel the tampon from the barrel at the selected tampon expulsion test rate as a function of the distance the tampon travels during expulsion to determine the work required to expel the tampon from the tampon applicator.

2. The method of claim 1 including the step of determining grip flex in the grip zone on the barrel of the tampon applicator during the step of expelling the tampon by using a force monitor.

3. The method of claim 2 wherein the step of determining grip flex in the grip zone includes using the force monitor to measure positive or negative forces at the grip zone as a result of any push back or collapse of the grip zone while the tampon is being expelled.

4. The method of claim 1 wherein the step of applying the force to the grip zone on the barrel of the tampon applicator is performed both before and during the step of applying the force to the plunger to expel the tampon at the selected tampon expulsion test rate.

5. The method of claim 1 wherein the step of calculating the force on the plunger as a function of the distance the tampon travels includes the step of measuring and recording the peak force reached during expulsion of the tampon at the selected tampon expulsion test rate.

6. The method of claim 1 wherein the step of calculating comprises forming a curve and including the step of measuring the area under the curve to determine the work required to expel the tampon at the selected tampon expulsion test rate.

7. The method of claim 1 wherein the step of calculating includes plotting the force on the plunger required to expel the tampon from the barrel at the selected tampon expulsion test rate as a function of the distance the tampon travels during expulsion to determine the work required to expel the tampon from the tampon applicator.

8. The method of claim 1, wherein the selected tampon expulsion test rate is 80 mm/sec.

9. A method for determining the work required to expel a tampon from a tampon applicator having a barrel containing the tampon and a plunger for expelling the tampon from the barrel, comprising the steps of:
    selecting a tampon expulsion test rate to be used to expel the tampon from the barrel of the tampon applicator;
    applying a force in the range of 400 to 1200 grams to the grip zone on the barrel of the tampon applicator;
    applying a force to the plunger sufficient to expel the tampon from the barrel of the tampon applicator at the selected tampon expulsion test rate;
    the step of applying the force to the grip zone on the barrel of the tampon applicator being performed at least during the step of applying the force to the plunger to expel the tampon from the tampon applicator at the selected tampon expulsion test rate;
    determining grip flex in the grip zone on the barrel of the tampon applicator during the step of applying the force to expel the tampon from the tampon applicator by using a force monitor; and
    calculating the force on the plunger required to expel the tampon from the barrel at the selected tampon expulsion test rate as a function of the distance the tampon travels during expulsion to determine the work required to expel the tampon from the tampon applicator.

10. The method of claim 9 including the step of measuring the actual gripping force used to grip the grip zone on the barrel of the tampon applicator in a clinical study of a selected number of consumers to establish a range of actual gripping forces and selecting an applicator gripping test force to be used to grip the grip zone based upon the range of actual gripping forces.

11. The method of claim 9 including the step of measuring the actual tampon expulsion rate used to expel the tampon from the barrel of the tampon applicator in a clinical study of a selected number of consumers to establish a range of actual tampon expulsion rates and selecting a tampon expulsion test rate to be used to expel the tampon within the range of actual tampon expulsion rates.

12. The method of claim 9 wherein the step of determining grip flex in the grip zone includes using the force monitor to measure positive or negative forces at the grip zone as a result of any push back or collapse of the grip zone while the tampon is being expelled.

13. The method of claim 9 wherein the step of calculating the force on the plunger as a function of the distance the tampon travels includes the step of measuring and recording the peak force reached during expulsion of the tampon at the selected tampon expulsion test rate.

14. The method of claim 9 wherein the step of calculating includes plotting the force on the plunger required to expel the tampon from the barrel at the selected tampon expulsion test rate as a function of the distance the tampon travels during expulsion to determine the work required to expel the tampon from the tampon applicator.

15. The method of claim 9, wherein the selected tampon expulsion test rate is 80 mm/sec.

* * * * *